United States Patent
Ballantyne

Patent Number: 5,185,005
Date of Patent: Feb. 9, 1993

[54] METHOD AND APPARATUS FOR SECURING A NASOGASTRIC TUBE

[75] Inventor: Alando J. Ballantyne, Houston, Tex.

[73] Assignee: Board of Regents, The University of Texas System, Austin, Tex.

[21] Appl. No.: 710,060

[22] Filed: Jun. 4, 1991

[51] Int. Cl.⁵ .............................................. A61M 5/32
[52] U.S. Cl. ............................... 604/174; 128/207.18; 128/DIG. 26; 604/179
[58] Field of Search ............... 604/174, 175, 177, 179, 604/54, 93, 264; 128/DIG. 26, 207.18; 606/108

[56] References Cited

U.S. PATENT DOCUMENTS

| | | | |
|---|---|---|---|
| 3,161,199 | 12/1964 | Shaw | 604/179 |
| 3,568,678 | 3/1971 | Pouquier et al. | 604/174 |
| 3,977,407 | 8/1976 | Coleman et al. | 604/179 |
| 4,284,076 | 8/1981 | Hall | 128/207.18 |
| 4,480,639 | 11/1984 | Peterson et al. | 604/179 |
| 4,658,814 | 4/1987 | Anderson | 604/179 |
| 4,778,448 | 10/1988 | Meer | 604/174 |
| 4,795,442 | 1/1989 | Traflet | 604/174 |
| 4,804,374 | 2/1989 | Laskody | 604/180 |
| 4,932,943 | 6/1990 | Nowak | 604/180 |

*Primary Examiner*—Gene Mancene
*Assistant Examiner*—Jeffrey A. Smith
*Attorney, Agent, or Firm*—Arnold, White & Durkee

[57] ABSTRACT

A nasogastric tube anchor, and a method of its use employing a bridle which passes through the patient's nostrils and nasopharynx, the ends of the bridle being fastened to a nasogastric tube exterior to the patient's nose to anchor said tube against undesired movement relative to the patient's nostril. Installation tools and methods are provided for positioning said bridle within the patient's nose such that one end of the bridle extends from each nostril.

17 Claims, 2 Drawing Sheets

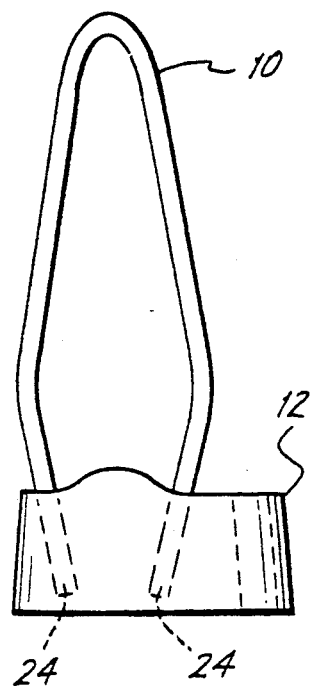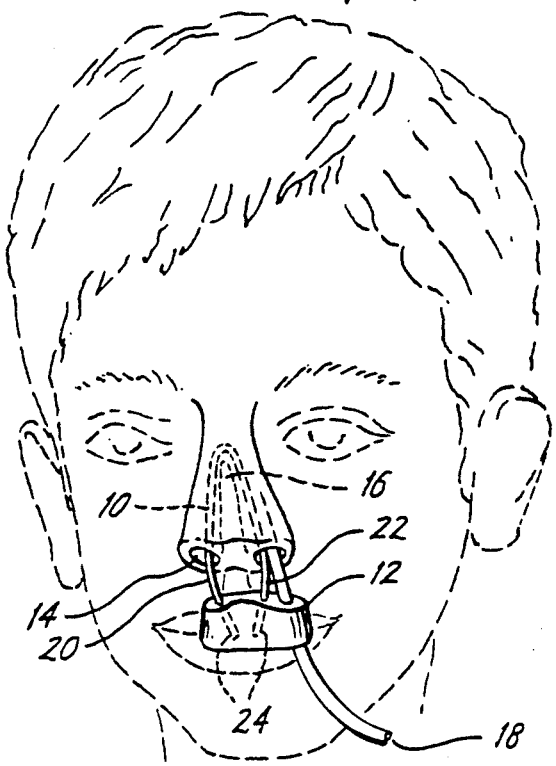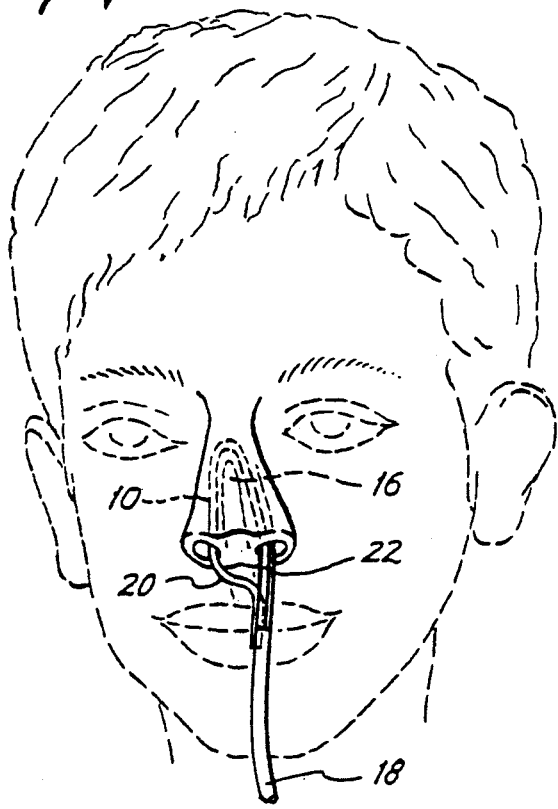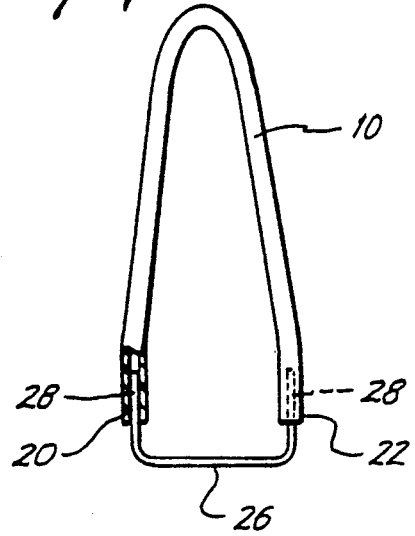

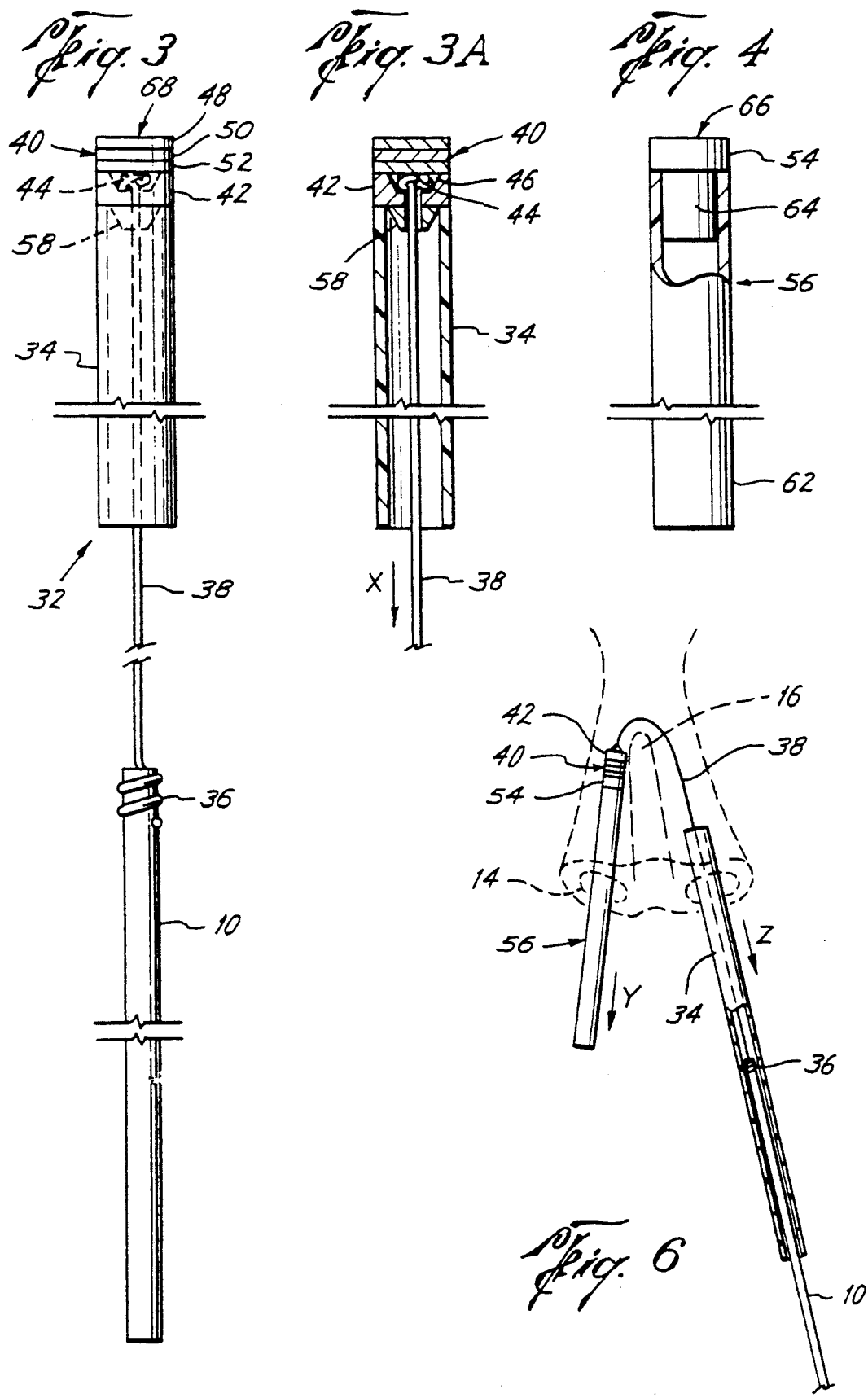

METHOD AND APPARATUS FOR SECURING A NASOGASTRIC TUBE

BACKGROUND OF THE INVENTION

II. Field of the Invention

This invention relates to an apparatus which is used to anchor a nasogastric tube external to the nose. In particular, the apparatus employs an elongated flexible member which passes through one nostril, around the posterior nasal septum, and out the other nostril. The two ends of the flexible member, one passing out each nostril, are attached to a nasogastric tube or are affixed to an anchoring clip, to which also may be anchored a nasogastric tube. The invention also includes an apparatus and method for installing the elongated flexible member through the patient's nose to pass around the nasal septum.

II. Description of Related Art

In the medical treatment of patients it is common practice to use a nasogastric tube for entering the gastrointestinal tract of the patient by initially passing the tube into a nostril. While placement and operation of such tubes is quite common and effective, certain problems are recognized in the medical profession regarding efficient, safe and comfortable mounting or placement of such tubes, especially since such tubes are frequently maintained in their operative position for extended periods.

It is well recognized that conventional gastrointestinal tubes utilize securing means such as tape, sutures or complex headgear. The irritation and discomfort associated with such securement methods and devices may render many conventional devices unsuitable. A typical means for securing such a tube is to wrap adhesive around the outer surface of the tube and secure the same adhesive strip or material to the outer surface of the nose. This method is troublesome in that normal movement of the patient sometimes causes nasal septal ulcers and/or necrosis by causing excessive tube movement while the tube is in direct contact with an inner portion of the nose, such as when the tube is continuously repositioned or due to the normal movement of the patient.

Many conventional securing devices such as headgear or headband assemblies attempt to overcome problems of the type set forth above through the provision of specific anchoring or mounting structures. While operable for their intended function, numerous forms of these conventional devices have been found to be overly complicated or somewhat difficult or time consuming in their installation, maintenance or removal from the patient, thereby necessitating extensive nursing care for repositioning or readjusting the tube properly into its operative position.

The prior art consists primarily of tube anchoring devices which rely on adhesive means for connecting the anchoring device to the patient's nose, or which rely on some sort of strap encircling the head to hold the securing device in its proper position. Devices incorporating adhesive means include those described in patents issued to Liskody, U.S. Pat. No. 4,804,374, and Nowak, U.S. Pat. No. 4,932,943. Patents disclosing devices which utilize a strap around the patient's head include Hall, U.S. Pat. No. 4,284,076, and Coleman et al., U.S. Pat. No. 3,977,407.

Both adhesive and head-band type securements can be easily removed by a belligerent patient, and prolonged use of adhesive tape can cause skin irritation. Furthermore, it is possible for these securement devices to hold the tube too securely. Some amount of normal movement of the tube relative to the nose and nostril through which it enters is desired. However, excessive movement relative thereto is to be prevented so as to reduce the possibility of ulcers or irritation to portions of the nose, skin, etc. disposed in direct contact with the adhesive tape or tube.

The above discussion points out the need for a method to securely anchor a transnasal tube, such as e.g. a nasogastric tube, at the point where it exits the patient's body through a nostril. There is particular need for such a method which will effectively resist the efforts of an uncooperative or belligerent patient to withdraw or excessively move the tube, and which avoids the other problems associated with adhesive and headband type securements.

SUMMARY OF THE INVENTION

The claimed invention comprises an apparatus for anchoring a tube such as a nasogastric tube which extends into a patient's nostril, more particularly comprising an elongated flexible bridle with two ends, one end protruding from each nostril, operatively positioned from one nostril, through the nasopharynx beyond the posterior nasal septum and out the other nostril, and means connected to said two ends of the bridle external to said nostrils for anchoring the tube relative to the nostril. The bridle may be constructed of a suitable elongated flexible material in the form of, for example, a tube, tape, ribbon, or cable.

The anchoring means, with which the nasogastric tube is anchored, may, for example, comprise an anchoring clip removably attachable to the two ends of the bridle, said anchoring clip having an outer surface upon which the tube can be connected, or having a bore or other structure which grips or holds the tube to be anchored. Said anchoring means may alternatively comprise, for example, a piece of material such as tape or string which is used to tape or tie together the protruding ends of the bridle and the nasogastric tube.

The anchoring clip may, for example, comprise simply a properly bent piece of wire or rod sized such that the two ends of a tubular bridle may be securely positioned over the two ends of said wire or rod with a fit that is tight enough to inhibit removal of the wire or rod from the bridle. In another embodiment, the anchoring means may comprise a clip removably attachable in other ways to the two ends of the bridle. Such a clip may also comprise a bore or other structure for receiving the nasogastric tube to be anchored. Such clip may further comprise two members which are designed to be snap fitted together with the two ends of the bridle seized between them to rigidly hold the ends of the bridle. Any of the above described anchoring means may be constructed to be either permanently or removably attachable to the ends of the bridle.

The claimed invention further comprises an apparatus providing means for operatively positioning the bridle through a patient's nose such that it passes through the nasopharynx and around the posterior nasal septum such that one end protrudes from each nostril. This apparatus comprises two installation tools.

In a preferred embodiment, a pulling cord is utilized, one end of which is affixed to a first magnet and the other end of which is affixed to one end of the bridle. The bridle and pulling cord are then slidably inserted through the first installation tool until the magnet is pulled flush against the distal end of said tool. The first magnet is held in place against the distal end of the first installation tool by tension applied to the bridle and pulling cord which extend from the proximal end of said tool.

The second installation tool has a second magnet securely attached to its distal end. Both installation tools and magnets are sufficiently rigid and sized so as to be slidable into a patient's nostrils to a point in the nasopharynx beyond the posterior nasal septum. This positioning apparatus further comprises means for inserting the distal end of the first installation tool, complete with the first magnet, within one nostril, and for inserting the distal end of the second installation tool, complete with the second magnet, within the other nostril such that the magnets positioned by each installation tool magnetically couple behind the posterior nasal septum.

Alternatively, in another embodiment, the pulling cord is omitted and the leading end of the bridle is directly attached to the first magnet. The bridle is then inserted through the first installation tool until the first magnet is held in place against the distal end of said installation tool prior to insertion of the tool into the nostril.

In either of the above described embodiments, both magnets may comprise one or more permanent magnets, or one or more permanent magnets combined with ferromagnetic material, to provide adequate magnetic force to effect the coupling of the magnets within the nasopharynx and to enable both magnets, magnetically coupled together, to be pulled from the patient's nostril.

Also claimed is a method for anchoring a tube extending into a patient's nose, comprising passing one end of a bridle into one nostril, around the posterior nasal septum, and out the other nostril, one end of said bridle extending from each nostril exterior to the patient's nose, fastening the two ends of the bridle to one another with an anchoring clip or otherwise, and securing a nasogastric tube extending into one of the patient's nostrils to the bridle ends or to the anchoring clip.

The claimed method of inserting the bridle into the patient's nose may further comprise the steps of connecting a proximal end of a pulling cord to the bridle, placing a distal end of the pulling cord into one of the patient's nostrils to a point beyond the posterior nasal septum, and pulling the pulling cord around the posterior nasal septum and out the other nostril, such that the bridle is installed in the patient's nose passing behind the posterior nasal septum with one end extending out each nostril. The distal end of the pulling cord may be placed within the first nostril by positioning it with a first installation tool which is removably inserted within the nostril. The pulling cord may be pulled around the posterior nasal septum and out the second nostril by the use of a second installation tool comprising means to couple the end of the pulling cord inserted into the first nostril to the end of the second installation tool, enabling the leading end of the pulling cord to be pulled out of the second nostril by removing the second installation tool from the second nostril.

Said coupling may comprise magnetic coupling of one magnet attached to the leading end of the pulling cord and one magnet fastened to the distal end of the second installation tool, which magnets are placed into close proximity in the nasopharynx beyond the posterior nasal septum such that they couple by magnetic force.

Both of the magnets involved may comprise permanent magnets or combinations of permanent magnets and ferromagnetic material. These methods for inserting the bridle into the patient's nose may be performed with the bridle itself directly attached to the first magnet, omitting the pulling cord connecting the leading end of the bridle to the first magnet.

Finally, the claimed invention comprises a method for anchoring a tube extending into a patient's nostril comprising inserting a bridle within a patient's nose by the methods discussed above or otherwise, and further comprising connecting an anchoring clip to both ends of said bridle, inserting the tube to be anchored into the patient's nostril and then securing that tube to the anchoring clip. Alternatively, the ends of the bridle and the tube may be securely joined together by, for example, tying with tape or string, or by gluing.

The present invention therefore provides an improved device and method which allows anchoring of a tube, such as a nasogastric tube, in a generally fixed position relative to the nostril by which it enters the patient's body. This invention avoids the problems associated with conventional means for anchoring such a tube, including discomfort, the need for replacing and repositioning, and efforts by belligerent patients to move or remove a transnasal tube. These and other advantages of the present invention will be further appreciated from the drawings and the detailed description provided below.

BRIEF DESCRIPTION OF THE DRAWINGS

So that the manner in which the above-recited advantages and features of the present invention, as well as others which will become apparent, are attained and can be understood in detail, a more particular description of the invention summarized above may be had by reference to the embodiment thereof which is illustrated in the appended drawings, which drawings form a part of this specification.

It is to be noted, however, that the appended drawings illustrate only typical embodiments of the invention and are therefore not to be considered limiting of its scope, for the invention may admit to other equally effective embodiments.

FIG. 1 is a frontal elevation view of an embodiment of an assembled nasogastric tube anchor.

FIG. 2 is a frontal elevation view of an assembled nasogastric tube anchor of the present invention installed on a patient in its operative position.

FIG. 2A is a frontal elevation view of an alternative embodiment of an assembled nasogastric tube anchor of the present invention installed on a patient in its operative position.

FIG. 3 illustrates a first installation tool used to install the bridle of the present invention, complete with bridle, pulling cord, and magnetic member.

FIG. 3A is a lateral cross-sectional view of a first installation tool used to install the present invention.

FIG. 4 illustrates a second installation tool used to install the bridle of the present invention.

FIG. 5 is a frontal elevation view of another embodiment of an assembled nasogastric tube anchor.

FIG. 6 illustrates the method of installation of a bridle in a patient's nose after the magnets have coupled together and during withdrawal of the first installation tool.

DESCRIPTION OF THE PREFERRED EMBODIMENTS

Referring to FIGS. 1 and 2, the nasogastric tube anchor of this invention in the embodiment illustrated comprises bridle 10 and anchoring clip 12. Bridle 10 comprises an elongated flexible member which passes through both nostrils 14 and around the posterior nasal septum 16 of a patient who requires the use of a nasogastric or other tube 18. The ends 20, 22 of bridle 10 extend from the patient's nostrils 14, where they are secured to bridle attaching means 24 of anchoring clip 12. Nasogastric tube 18 is also attached to anchoring clip 12 by, for example, being passed through a bore in anchoring clip 12 which is adapted to securely grip said tube.

The assembly comprising bridle 10 and anchoring clip 12 operates to secure nasogastric tube 18 in a desired position relative to a patient's nose, allowing minimal normal movement of tube 18, without requiring adhesive, suture or other attachment to the skin of the face and without requiring a band around the head. This invention is particularly well suited to be used on a belligerent patient, as it is designed to be more difficult to remove than other tube anchoring devices.

This nasogastric tube anchor can be easily adapted to securely anchor any tube or other apparatus which must be maintained in a position extending from a patient's nose.

The assembly comprising bridle 10 and anchoring clip 12 constitutes a continuous loop encircling the patient's nasal septum which cannot be removed inadvertently by movement of the patient, nor by the efforts of a belligerent patient. It can, however, be easily removed by medical personnel by severing bridle 10 with scissors or by manipulation of anchoring clip 12. Bridle 10 is formed of a flexible elastomer, fabric, or other material, chosen for flexibility, softness, tensile strength and non-irritating qualities. It can take any convenient form, such as, for example, a tube, tape, cable or monofilament.

As shown in FIG. 5, anchoring clip 26 in one preferred embodiment may consist of an appropriately bent rod, constructed of, for example, stainless steel, whose upturned ends 28 are configured to receive the ends of bridle 10. In this embodiment, bridle 10 is tubular, and the diameter of rod 26 is selected such that its ends 28 can be slidably inserted into the ends 20, 22 of bridle 10. By proper material selection and treatment, for example by knurling ends 28 or use of adhesives, it can be made very difficult in this embodiment to remove a bridle end from its attachment. A nasogastric tube is attached to anchoring clip 26 by, for example, taping. Alternatively, the anchoring clip can be omitted altogether and the ends 20, 22 of bridle 10 can be secured together and to tube 18 by alternative anchoring means. For example, ends 20, 22 of bridle 10 can be glued to tube 18, as illustrated in FIG. 2A, or ends 20, 22 can be tied or taped together and to tube 18 with string, tape, or other suitable material.

A method for installing the nasogastric tube anchor of this invention is described with reference to FIGS. 3 and 4.

FIG. 3 illustrates first installation assembly 32. First installation tool 34 comprises an adequately rigid tube sized to be slidable over bridle member 10, yet narrow enough to be easily insertable into a nostril such that the distal end 68 of first installation assembly 32 resides within the nasopharynx beyond the posterior nasal septum. Installation assembly 32 comprises bridle 10 to which is tied, e.g. with a needle knot 36, a trailing end of pulling cord 38. Pulling cord 38 and bridle 10 can be connected by means other than a needle knot 36, which includes but is not limited to use of adhesives, tape or fabrication of pulling cord 38 and bridle 10 from a single piece of material. Pulling cord 38 can be a flexible monofilament string, such as, for example, fishing line.

The leading end of pulling cord 38 is secured to magnetic member 40. Magnetic member 40 is disk shaped and has a diameter approximately equal to that of the outside diameter of first installation tool 34, for example, about 5 mm. In a preferred embodiment, fastening plate 42 comprises a steel disk that is drilled and preferably countersunk. The leading end of pulling cord 38 is shown inserted through the drilled hole from the non-countersunk side of fastening plate 42, knotted and trimmed such that knot 44 fits into the counter-sunk cavity 46 (FIG. 3A) without pulling out of the drilled hole. Countersunk cavity 46 is then filled flush with epoxy to further secure cord 38 to fastening plate 42. Magnets 48, 50, 52 (e.g., three dental magnets) are glued to the leading face of fastening plate 42 to make up magnetic member 40. When connected together as shown in FIG. 3, magnets 48, 50, and 52 have sufficient magnetic force to maintain magnetic coupling with magnet 54 of assembly 56 described below. Sumarium Cobalt JobMax #18 (5 mm.×1.5 mm.) magnets have been successfully used for magnets 48, 50, 52 and 54. Of course, the described configuration of assembly 32 is exemplary only and can be replaced by other suitable configurations as would be apparent to one skilled in the art.

The leading end of pulling cord 38 is attached to magnetic member 40 and the trailing end of pulling cord 38 is attached to bridle 10. The trailing end of bridle 10 is inserted into the distal end of and through first installation tool 34. Bridle 10 and pulling cord 38 are pulled through first installation tool 34 until fastening plate 42 is flush against the distal end of installation tool 34, where it is held by tension applied in direction X to pulling cord 38 external to the proximal end of installation tool 34, as illustrated in FIG. 3A. In a preferred embodiment, an epoxy cone 58 is constructed on the trailing face of fastening plate 42 around cord 38. When fastening plate 42 is pulled against the distal end of first installation tool 34, cone 58 enters the distal end of said tool and centers fastening plate 42 thereon.

Alternatively, the first installation assembly can be assembled without a pulling cord. In such an embodiment, the leading end of bridle member 10 itself is directly attached to magnetic member 40, for example, by providing a fastening plate 42 which is drilled and countersunk such that the leading end of bridle 10 can be inserted through the drilled hole and knotted, such that knot 60 fits within the countersunk cavity but does not pull through the drilled hole. This embodiment is constructed and operated in the same manner as is the embodiment described above, except that no pulling cord is present between magnetic member 40 and the leading end of bridle 10.

Referring to FIG. 4, second installation assembly 56 comprises adequately rigid member 62 with one or more permanent magnets 54, 64 preferably permanently affixed to the 'istal end thereof. Magnet 54 is oriented such that its outwardly facing surface 66 is magnetically attractive to outwardly facing surface 68 of magnetic member 40 of first installation assembly 32. Second installation assembly 56 is sized to permit it to be easily inserted into a patient's nostril sufficiently to position magnet 54 beyond the posterior nasal septum. Magnet 64 may be a stirring magnet inserted lengthwise into the distal end of rigid member 62 and fastened into position. Magnet 54 may be a dental magnet attached to the distal end of rigid member 62 and magnet 64, for example by gluing. Magnet 64 is oriented to act in series with magnet 54.

Rigid members 34, 62 of first installation assembly 32 and second installation assembly 56 may, for example, comprise suction catheter tubes of suitable diameter and cut to the desired length.

Referring to FIGS. 3 and 4, in a preferred embodiment, bridle 10 is installed in a patient's nose by a method comprising inserting the distal end 68 of first installation assembly 32 into a first nostril of the patient until magnetic member 40 is positioned beyond the posterior nasal septum. The distal end 66 of second installation assembly 56 is then inserted into a second nostril of the patient until magnet 54 is beyond the posterior nasal septum, in close proximity to magnetic member 40. When this configuration is achieved, pulling cord 38 extending from the proximal end of first installation tool 34 is released, allowing magnetic member 40 to be pulled by magnetic force toward and to couple with magnet 54. At this point the two magnets, 40 and 54, are coupled together by magnetic force. When the magnets magnetically couple within the nasopharynx an audible click can be heard as the magnets slap together, which click serves to verify proper placement of the tools.

Referring to FIG. 6, first installation tool 34 is withdrawn in direction Z from the nostril, while pulling cord 38 and bridle 10 are allowed to slide through tool 34 as it is withdrawn. Tool 34 is slidably removed over cord 38 and bridle 10 until it is entirely separated from cord 38 and bridle 10. Second installation tool 56 is then withdrawn from the second nostril in direction Y, pulling with it magnetic member 40 with the leading end of pulling cord 38 attached thereto. As second installation tool 56 and the leading end of pulling cord 38 are withdrawn from the second nostril, the trailing end of pulling cord 38 and the leading end of bridle 10 enter the first nostril. When second installation tool 56 is entirely removed from the second nostril, pulling cord 38 can be grasped and bridle 10 pulled into its proper position by exertion of tension on pulling cord 38, pulling the leading end of bridle 10 into the first nostril, around the posterior nasal septum, and down through the second nostril until it passes out of the nasal opening.

Alternatively, first installation tool 34 can be left in place in the nostril, or partially withdrawn, after the magnets have coupled, while second installation tool 56 and pulling cord 38 are pulled from the second nostril to draw bridle 10 into first installation tool 34, around the posterior nasal septum, and further into its operative position with the leading end of bridle 10 external to the second nostril. First installation tool 34 is then removed from the nostril, while the portion of bridle 10 remaining inside said tool slides relative to said tool and retains its position in the nose. In this way first installation tool 34 may operate to shield nasal tissues from abrasion and irritation while bridle 10 is pulled into position.

Referring to FIGS. 2 and 2A, once bridle 10 is positioned in the patient's nose with ends 20, 22 extending from each nostril 14, both ends 20, 22 of bridle 10 are cut to the desired length and trimmed to fit bridle attachment means 24, 24 of anchoring clip 12. Both ends 20, 22 of bridle 10 are then attached to clip 12, which comprises anchoring means for attachment to nasogastric tube 18 which is inserted through one of the patient's nostrils 14.

Bridle attachment means 24, 24 may be of any suitable construction which allows attachment of bridle ends 20, 22 while inhibiting or preventing withdrawal of bridle ends 20, 22 once they have been inserted or attached. Such means may incorporate, e.g., pinch rollers or levers, or barbs, which permit "one-way" movement of the bridle ends into or onto clip 12. In another embodiment, anchoring clip 12 comprises two pieces which are snap-fitted together upon the ends 20, 22 of bridle 10 and perhaps also upon tube 18. The ends 20, 22 and tube 18 are secured within such a clip, e.g., by compression and friction means.

Referring to FIG. 5, in a preferred embodiment the tubular ends of bridle 10 are slid over bridle attachment means 28 of clip 26. Bridle attachment means 28 are, for example, stainless steel rod segments selected to be insertable tightly into the ends 20, 22 of bridle 10. In this embodiment, a nasogastric tube (e.g. 18) may be anchored by suitable means of attachment to the center portion of anchoring clip 26, e.g. by taping.

In yet other embodiments, for example, the ends 20, 22 of the bridle extending from the nostrils and the nasogastric tube being anchored may be glued together (FIG. 2A), or they may be tied or taped together with e.g. string, umbilical tape, or adhesive tape.

Further modifications and alternative embodiments of the apparatus and method of this invention will be apparent to those skilled in the art in view of this description. Accordingly, this description is to be construed as illustrative only and is for the purpose of teaching those skilled in the art the manner of carrying out the invention. It is to be understood that the forms of the invention herein shown and described are to be taken as the presently preferred embodiments. Various changes may be made in the shape, size and arrangement of parts. For example, equivalent elements or materials may be substituted for those illustrated and described herein, parts may be reversed, and certain features of the invention may be utilized independently of the use of other features, all as would be apparent to one skilled in the art after having the benefit of this description of the invention.

What is claimed is:

1. An apparatus for anchoring a nasogastric tube, comprising:
    an elongated flexible bridle having first and second ends, the bridle adapted to by inserted around a patient's nasal septum with one of said first and second ends extending outwardly from each of the patient's nostrils;
    first means adapted to releasably couple to the first end of the bridle for inserting the first end of the bridle into a patient's first nostril to a point beyond the nasal septum; and
    second means insertable through a patient's second nostril adapted to engage the first end of the bridle and for pulling the first end of the bridle exterior to the patient's second nostril.

2. An apparatus providing means for operatively positioning a bridle through a patient's nostrils, comprising:
    a pulling cord having a distal end and a proximal end, said distal end attached to at least one first magnetic member and said proximal end attached to said bridle;

a first installation tool having an inside dimension slidable over said bridle and said pulling cord, said tool having a distal end configured to releasably retain said first magnetic member and said pulling cord extending within said tool;

a second installation tool having a distal end and a proximal end, said distal end having a second magnetic member connected thereto; and means for inserting the distal end of said first installation tool within one nostril and the distal end of said second installation tool within the other nostril, whereby the magnetic members at the distal ends of said tools magnetically couple behind the posterior nasal septum.

3. An apparatus providing means for operatively positioning a bridle through a patient's nostrils, comprising:

a bridle having a distal end and a proximal end, said distal end attached to at least one first magnetic member;

a first installation tool having an inside dimension slidable over said bridle, said tool having a distal end configured to releasably retain said first magnetic member;

a second installation tool having a distal end and a proximal end, said distal end having a second magnetic member connected thereto; and means for inserting the distal end of said first installation tool within one nostril and the distal end of said second installation tool within the other nostril, whereby the magnetic members connected to the distal ends of said tools magnetically couple behind the posterior nasal septum.

4. The apparatus of claim 2 or 3, wherein said magnetic members comprise permanent magnets.

5. A nasogastric tube anchoring kit, comprising:

a bridle having first and second ends, the bridle adapted to be operatively positioned around a patient's posterior nasal septum with one of said ends protruding from each of a patient's first and second nostrils;

an installation tool adapted to insert the first end of the bridle into a first nostril to a point beyond a posterior nasal septum; and a retrieval tool adapted to be inserted into a second nostril to a point beyond the posterior nasal septum and further adapted to engage the first end of the bridle and to pull the first end of the bridle out through the second nostril.

6. A nasogastric tube anchoring kit, comprising:

a bridle having first and second ends, the bridle adapted to be operatively positioned around a patient's posterior nasal septum with one of said ends protruding from each of a patient's first and second nostrils;

a pulling cord having a leading end and a trailing end, the trailing end adapted to be connected to the first end of the bridle;

an installation tool adapted to insert the leading end of the pulling cord into a first nostril to a point beyond the posterior nasal septum;

a retrieval tool adapted to be inserted into a second nostril to a point beyond the posterior nasal septum and further adapted to engage the leading end of the pulling cord and to pull the leading end of the pulling cord out through the second nostril.

7. A method for anchoring a tube extending into a patient's nose, comprising:

passing a first end of a bridle having first and second ends into one nostril past the posterior nasal septum, and retrieving said first end through the other nostril such that the first and second ends of said bridle extend from the patient's nostrils exterior to said nose; and connecting said first and second ends of the bridle to said tube.

8. A method for anchoring a tube extending into a patient's nose, comprising:

passing a first end of a bridle having first and second ends into one nostril past the posterior nasal septum, and retrieving said first end through the other nostril such that the first and second ends of said bridle extend from the patient's nostrils exterior to said nose;

fastening a clip to said first and second ends of the bridle; and securing said tube extending into said nose onto said clip.

9. A method for anchoring a tube extending into a patient's nostril, comprising:

providing a pulling cord having a trailing end connected to a bridle;

connecting the leading end of said pulling cord to a magnet placed at the distal end of a first installation tool;

providing a second installation tool having a distal end and a proximal end, said distal end including a magnet;

inserting the distal end of said first installation tool within a first nostril and the distal end of said second installation tool within a second nostril such that said magnets at said distal ends are magnetically coupled at a point beyond the posterior nasal septum;

pulling said second installation tool and magnetically coupled said pulling cord and attached bridle around the posterior nasal septum such that the ends of said bridle extend external to each nostril;

inserting said tube into the patient's nostril and securing said tube to said ends.

10. The method of claim 9, wherein said first installation tool is withdrawn from said first nostril slidably over said pulling cord and said bridle after coupling occurs and before said second installation tool is pulled from said other nostril.

11. A method for anchoring a tube extending over a patient's nose, comprising:

passing one of a bridle into one nostril, around the posterior nasal septum, and out the other nostril of said nose such that one end of said bridle extends from each nostril exterior to said nose, this passing step further comprising:

connecting a trailing end of a pulling cord to a leading end of said bridle;

placing a leading end of said pulling cord within a first nostril to a point beyond beyond the posterior nasal septum; and pulling said pulling cord around said posterior nasal septum such that the leading end of said bridle enters said first nostril, passes around the posterior nasal septum, and exits a second nostril; and connecting said two ends of the bridle to said tube.

12. The method as recited in claim 11, wherein said placing step comprises positioning said leading end with a first installation tool removably inserted within said nostril.

13. A method for anchoring a tube extending into a patient's nose, comprising:
- passing one end of a bridle into one nostril, around the posterior nasal septum, and out the other nostril of said nose such that one end of said bridle extends from each nostril exterior to said nose, this passing step further comprising:
  - connecting a trailing end of a pulling cord to a leading end of said bridle;
  - placing a leading end of said pulling cord within a first nostril to a point beyond the posterior nasal septum; and
  - pulling said pulling cord around said posterior nasal septum such that the leading end of said bridle enters said first nostril, passes around the posterior nasal septum, and exits a second nostril;
- fastening a clip to said two ends of the bridle; and
- securing said tube extending into said nose onto said clip.

14. The method as recited in claim 13, wherein said placing step comprises positioning said leading end with a first installation tool removably inserted within said nostril.

15. The method as recited in claim 11 or 13, wherein said pulling step comprises:
- providing a retrieval tool having a distal end and a proximal end;
- inserting the distal end of said retrieval tool within the other nostril;
- coupling the leading end of said pulling cord to the distal end of said retrieval tool; and
- pulling said retrieval tool with the pulling cord coupled thereto out of said other nostril.

16. The method as recited in claim 15, wherein said coupling step comprises magnetic coupling, one magnetic member being fastened to the leading end of said pulling cord and one magnetic member being fastened to the distal end of said retrieval tool.

17. The method of claim 16, wherein both magnetic members comprise permanent magnets.

* * * * *

UNITED STATES PATENT AND TRADEMARK OFFICE
CERTIFICATE OF CORRECTION

PATENT NO.   :   5,185,005

DATED        :   February 9, 1993

INVENTOR(S)  :   Alando J. Ballantyne

It is certified that error appears in the above-identified patent and that said Letters Patent is hereby corrected as shown below:

Column 10, line 51 (claim 11), "over" should be --into--.

Column 10, line 53 (claim 11), after the first occurrence of the word "one", insert the word --end--.

Signed and Sealed this

Twenty-third Day of November, 1993

Attest:

BRUCE LEHMAN

Attesting Officer

Commissioner of Patents and Trademarks